United States Patent [19]

Witkowski et al.

[11] 3,976,545

[45] Aug. 24, 1976

[54] 1,2,4-TRIAZOL E-3-CARBOXAMIDES AS ANTIVIRAL AGENTS

[75] Inventors: Joseph T. Witkowski, Laguna Niguel; Roland K. Robins, Santa Ana, both of Calif.

[73] Assignee: ICN Pharmaceuticals, Inc., Irvine, Calif.

[22] Filed: Sept. 29, 1975

[21] Appl. No.: 617,432

Related U.S. Application Data

[60] Division of Ser. No. 340,332, March 12, 1973, Pat. No. 3,927,216, which is a continuation-in-part of Ser. No. 240,252, March 31, 1972, Pat. No. 3,798,209, which is a continuation-in-part of Ser. No. 149,017, June 1, 1971, abandoned.

[52] U.S. Cl. ............................... 195/28 N; 195/29

[51] Int. Cl.$^2$.......................................... C12D 13/06
[58] Field of Search ............................ 195/28 N, 29

[56] References Cited
UNITED STATES PATENTS 3,535,207   10/1970   Shiro et al. ..................... 195/28 N

*Primary Examiner*—Alvin E. Tanenholtz
*Attorney, Agent, or Firm*—Kay H. Boswell

[57] ABSTRACT

The use of 1,2,4-triazole-3-carboxamide and 1,2,4-triazole-3-thiocarboxamide and physiologically compatible salts thereof as antiviral agents is disclosed. A process for synthesizing 1-β-D-ribofuranosyl-1,2,4-triazole-3-carboxamide is also disclosed.

5 Claims, No Drawings

1,2,4-TRIAZOLE-3-CARBOXAMIDES AS ANTIVIRAL AGENTS

This application is a division of application Ser. No. 340,332, filed Mar. 12, 1973, now U.S. Pat. No. 3,927,216 which issued on Dec. 16, 1975, which in turn is a continuation in part of application Ser. No. 240,252, filed Mar. 31, 1972, which issued as U.S. Pat. No. 3,798,209 on Mar. 19, 1974, which in turn is a continuation in part of Ser. No. 149,017, filed June 1, 1971, now abandoned.

BACKGROUND OF THE INVENTION

During the past decade, many nucleoside analogs have been found to exhibit good antitumor and antiviral activities. Among the presently known synthetic nucleosidic antiviral agents, the more important generally are considered to be 5-iodo-2'-deoxyuridine (IDU), 9-β-D-arabinofuranosyladenine (ara-A), and 1-β-D-arabinofuranosylcytosine (ara-C). These compounds, however, are only active against a limited spectrum of viruses which does not include those causing respiratory diseases in man (influenza, common cold). The only nucleosidic analog of which we are aware that is active against these respiratory disease viruses is 1-β-D-ribofuranosyl-1,2,4-triazole-3-carboxamide which is described in our copending United States patent application, Ser. No. 240,252, filed Mar. 31, 1972, entitled 1,2,4-Triazole Nucleosides, which application is a continuation in part of Ser. No. 149,017, filed June 1, 1971, entitled 1,2,4-Triazole Nucleosides.

Certain derivatives of this latter compound have also been found to have significant activity against these viruses, and it has also been discovered that the triazole bases of certain of such compounds, 1,2,4-triazole-3-carboxamide and 1,2,4-triazole-3-thiocarboxamide, likewise have significant antiviral activity against these respiratory viruses. The chemical structure and synthesis of each compound has been previously reported (*Latvijas PSR Zinatnu Akad. Vestis*, Kim. Ser., 1965, (2) 204–208 See *Chem. Abst.* 63, 13243 (1965).

It has also now been discovered that 1,2,4-triazole-3-carboxamide may be caused to undergo enzymatic conversion to 1-β-D-ribofuranosyl-1,2,4-triazole-3-carboxamide, the aforenoted nucleoside which is a significantly effective antiviral compound. As will be shown hereinafter, the triazole base may be reacted with the enzyme Nucleoside Phosphorylase to effect the indicated conversion.

SUMMARY OF THE INVENTION

The present invention thus relates to the use of compounds of the following structure as antiviral agents:

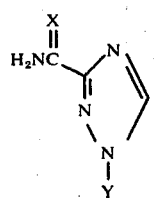

wherein X is O (in which case the compound is 1,2,4-triazole-3-carboxamide) or S (the compound is 1,2,4-triazole-3-thiocarboxamide), and Y is H, an alkalai metal or an amine. In the synthesis of 1-β-D-ribofuranosyl-1,2,4-triazole-3-carboxamide, the triazole base may be reacted with the enzyme Nucleoside Phosphorylase in accord with the appropriate conditions disclosed hereinafter.

DETAILED DESCRIPTION OF THE INVENTION

The carboxamide compounds may be prepared in accordance with the following examples in which temperatures and melting points are expressed in degrees Centigrade.

EXAMPLE I

3-Cyano-1,2,4-triazole

A mixture of triethyl orthoformate (150 ml) and 1-cyanoformidic acid hydrazide, K. Matsuda and L. T. Morin, *J. Org. Chem.*, 26:3783 (1961), (25.2 g, 0.30 mol) was cooled to 0° and a solution (4.0 ml) of dioxane saturated with anhydrous hydrogen chloride was added with stirring. The mixture was stirred with cooling in an ice bath for 5 hours and stirring at 25° was continued for 15 hours. The mixture was evaporated to dryness and ether (500 ml) was added to the residue. The solution was filtered, washed with water, and the organic layer was dried over magnesium sulfate. The solution was filtered and the ether was removed. Crystallization of the product from ethyl acetate-benzene provided 16.0 g (56.8%) of 3-cyano-1,2,4-triazole with a melting point of 185°–187°. All properties of the compound were identical with those of a sample prepared by the method of Cipens and Grinsteins, *Latvijas PSR Zinatnu Adad. Vestis.*, Kim Ser., 1965 (2), 204–208. *Chem Abst.*, 63, 13243 (1965).

Anal. Calcd. for $C_3H_2N_4$: C, 38.30; H, 2.14; N, 59.56. Found: C, 38.29; H, 1.98; N, 59.16.

EXAMPLE II 1,2,4-Triazole-3-carboxamide

Methyl 1,2,4-triazole-3-carboxalate was heated with excess aqueous ammonia until the reaction was complete. The mixture was cooled and the product was collected. Recrystallization from water afforded a nearly quantitative yield of 1,2,4-triazole-3-carboxamide with a melting point of 313°–315° dec.

Anal. Calcd. for $C_3H_4N_4O$: C, 32.14; H, 3.60; N, 49.99. Found: C, 32.37; H, 3.73; N, 50.09.

EXAMPLE III 1,2,4-Triazole-3-thiocarboxamide

A mixture of 3-cyano-1,2,4-triazole of Example I (4.7 g, 0.050 mol), ethanol (50 ml) and triethylamine (8.0 ml) was stirred at room temperature while hydrogen sulfide gas was bubbled into the mixture for 4 hours. The solvent was removed and water was added to the residue to provide 2.7 g of product. Recrystallization from water afforded pure 1,2,4-triazole-3-thiocarboxamide with a melting point of >350°.

Anal. Calcd. for $C_3H_4N_4S$: C, 28.12; H, 3.15; N, 43.72; S, 25.02. Found: C, 28.12; H, 3.18; N, 43.60; S, 25.09.

EXAMPLE IV 1,2,4-Triazole-3-carboxamide Sodium Salt

A solution consisting of 1,2,4-triazole-3-carboxamide (1.12 g, 10.0 mmol), sodium hydroxide (0.40 g, 10.0 mmol) and water (10.0 ml) was frozen and the sample was lyophilized. The product was obtained as the semihydrate of 1,2,4-triazole-3-carboxamide sodium salt with a melting point of >320°.

Anal. Calcd. for $C_3H_3N_4ONa \cdot 1/2\ H_2O$: C, 25.18; H, 2.82; N, 39.16; Na, 16.07. Found: C, 25.24; H, 2.78; N, 38.92; Na, 16.00.

Other physiologically acceptable alkali metal and amine salts such as the choline salt may be similarly prepared.

1,2,4-Triazole-3-carboxamide may be converted to 1-$\beta$-D-ribofuranosyl-1,2,4-triazole-3-carboxamide by reaction with the enzyme Nucleoside Phosphorylase at a pH within the range of about 5 to about 9, preferably 7 to 8, at an enzyme concentration of from about 0.015 to about 0.75 mg/ml, preferably about 0.15 mg/ml, and a temperature within the range of about 0° to about 50°C, with the preferred temperature being approximately 25° to about 35°C. Satisfactory results have been obtained when the triazole base is present in a concentration greater than $5 \times 10^{-5}$ M and ribose-1-phosphate is present at a concentration greater than $2 \times 10^{-5}$ M. Generally about 0.1 to about 2 hours, preferably about 0.5 to about 1 hour, are required for the reaction. The source of the enzyme may be animal, tissue, or bacteria. The principal bacterial sources are E. coli and yeast, while a variety of animal sources exist, including beef spleen, rat liver, calf liver, calf thymus, beef liver, monkey brain, horse liver, calf spleen, human erythrocytes, fish skin, and fish muscle.

The synthesis will be better understood from the following example.

EXAMPLE V

1$\beta$-D-Ribofuransyl-1,2,4-triazole-3-carboxamide

Synthesis of 1-$\beta$-D-ribofuranosyl-1,2,4-triazole-3-carboxamide from 1,2,4-triazole-3-carboxamide via Purified Calf Spleen Nucleoside Phosphorylase.

The incubation samples contained, in a final volume of 0.135 ml, tris HCl, pH 7.4, 50 $\mu$moles, ribose-1-phosphate, 0.25 $\mu$moles; 1,2,4-triazole-3-carboxamide ($H^3$), 42 $\mu c/\mu$mole, .05 $\mu$ moles; and calf spleen nucleoside phosphorylase (Sigma Chemical Co., St. Louis, Mo.), - 80 $\mu$g.

The samples were incubated at 25° for 5 minutes and then frozen in dry ice - isopropanol to stop the reaction. Aliquots of the thawed samples were then spotted on silica gel together with standard solutions of 1,2,4-triazole-3-carboxamide and 1-$\mu$-D-ribofuranosyl-1,2,4-triazole- 3-carboxamide and separated in isopropanol: $NH_4OH$: $H_2O$ (7: 1:2). Areas of the chromatograms coinciding with 1,2,4-triazole-3-carboxamide were removed and counted to determine the percent of conversion of 1,2,4-triazole-3-carboxamide to 1-$\beta$-D-ribofuranosyl-1,2,4-triazole-3-carboxamide.

| RESULTS OF NUCLEOSIDE PHOSPHORYLASE ASSAY WITH 1,2,4-TRIAZOLE-3-CARBOXAMIDE | |
| --- | --- |
| Sample | % Conversion |
| − enzyme | 0.8 |
| − ribose-1-P, + enzyme, 80$\mu$g | 1.1 |
| + enzyme, 20$\mu$g | 37.9 |
| + enzyme, 40$\mu$g | 48.4 |
| + enzyme, 60$\mu$g | 54.1 |

It is apparent from the foregoing that the indicated conversion occurred, with greater conversion achieved with greater concentration of enzyme.

When either 1,2,4-triazole-3-carboxamide or 1,2,4-triazole-3-thiocarboxamide is used as an antiviral agent, a quantity of from about 0.001 to about 10% by weight, normally about 0.001 to about 5%, and preferably about 0.01 to about 2.5%, based on total weight, of the agent will be used in an appropriate diluent, with the actual amount being dependent on a number of factors, namely severity of the infection, general health and age of the host, etc. In any event, the actual amount should be sufficient to provide a chemotherapeutically effective amount of the agent to the host in a convenient volume, which will be readily within the ability of those skilled in the art to determine given the disclosure herein.

In one form, the compounds may be used as an aerosol nasal spray, of the type described in U.S. Pat. No. 3,014,844, the disclosure of which is incorporated by reference herein, containing the indicated quantity of the antiviral compound suspended in a liquified propellant, such as a lower alkane (up to 5 carbon atoms), a lower alkyl chloride, or a fluorinated or fluorochlorinated lower alkane (available commercially under the trademark, "Freon"). Generally, the propellant is a gas at room temperature and atmospheric pressure, has a boiling point below about 65°F at atmospheric pressure, and of course, is nontoxic. Particularly suitable such propellants are dichlorodifluoromethane (Freon 12), dichlorotetrafluoroethane (Freon 14), and trichloromonofluoromethane (Freon 11). When used in the suspension, the antiviral agent should be finely divided, as for example, smaller than 100 microns diameter, preferably not greater than 25 microns and more preferably about 0.5 to 4 microns diameter. It may also be advantageous to include a surface active agent, preferably non-ionic, e.g., esters or partial esters of fatty acids containing 6 to 22 carbon atoms such as caproic, octoic, lauric, plamitic, stearic, linoleic, etc., to help avoid agglomeration of the powder. Normally, only a relatively small quantity of the surface active agent will be used, as for example, from about 0.1 to about 5% by weight, preferably from about 0.25 to about 1.0%, although larger quantities may be used if desired. Similarly, the stated quantity of the carboxamide antiviral agent may be dissolved in the liquified propellant with the aid of an appropriate solvent, as described in U.S. Pat No. 2,868,691, the disclosure of which is also incorporated by reference herein.

If desired, either of the antiviral agents may be injected into the host in which case it would be in the form of physiological saline solution or suspension containing from about 10 to about 500 milligrams of the agent per milliliter of solution.

The antiviral agents may be administered as oral preparations, in capsule or tablet form. The tablets or capsules will contain from about 10 to 500 milligrams of the compound per tablet or capsule. The required dose of the antiviral compounds, as noted above, will vary upon the condition of the patient, but will normally range from approximately 10 to 2000 milligrams per day. To effectively inhibit either RNA or DNA viruses, a concentration of about 32 micrograms of either compound per milliliter of serum is required. The capsules will be the usual gelatin capsules and will contain in addition to the antiviral agent in the quantity indicated above, a small quantity, for example less than 5% by weight, preferably less than 1.0%, magnesium stearate or other flowing agent, such as "Avicel" (carboxymethylcellulose). Tablets will contain the foregoing amount of the antiviral agent and a binder, which may be a gelatin solution, a starch paste in water, polyvinyl pyrilidone, polyvinyl alcohol in water, etc., with a typical sugar coating.

The antiviral agents also may be administered topically in an ointment, cream, emulsion or topical solution, depending on the condition of the viral skin infection to be treated, in which the antiviral agent, in the aforeindicated quantity, is formulated with the standard carriers and other ingredients commonly used for such topical applications. Thus, ointments, by reason of a greasy base, are recommended for chronic conditions, while creams, emulsions and topical solutions are recommended for acute and subacute lesions. Unlike ointments, creams are generally water soluble and exhibit vanishing properties. Emulsions are used of necessity where treatment with plural agents is indicated, one of which is insoluble in media in which the other may be dissolved, so that plural emulsified carrier phases are required for uniform distribution. "Topical solution" refers to a solution of active ingredients in a solvent material intermediate in viscosity between creams and easily evaporable solvents like alcohol, so that a balance of spreadability and prolongation of action is achieved.

As exemplary of the many topical ointment, cream, and solution formulations which may be generally applied are the following combinations of materials:

Ointments a. Petroleum without excipients.
b. Plastibase, a plasticized hydrocarbon gel available from Squibb, Inc. and comprised of polyethylene and mineral oil.

Creams a. Methyl paraben USP
   Propyl paraben USP
   Spermaceti USP
   Sodium lauryl sulfate USP
   Stearyl alcohol USP
   Cotyl alcohol USP
   Glycerin USP
   Deionized water
b. Stearic acid
   Propylene glycol
   Sorbitan monostearate and oleate
   Polyoxyethylene sorbitan monostearate
   Citric acid
   Methyl and propyl parabens
c. Water base
   Potassium sorbate
   Methyl and propyl parabens
   Glycerol monostearate
   Squalane
   Polysorbate 80 (USP)
   Spermaceti
   Stearyl alcohol
   Sorbital solution
d. Polyethylene glycol 400 (USP)
   Propylene glycol
   Carboxymethylene
   Monoamylamine
   Titanium dioxide
   Butylated hydroxytoluene Topical Solutions a. Polyvinyl alcohol-water
b. Polyethylene glycol 400

Accordingly, then, the topical vehicles are commonly comprised of, in addition to bodying agents, humectants, saponifying agents, emulsifiers, solvents, penetrants, pH regulators, plasticizers, emollients, preservatives, hardening agents, pigments, and perfumes, all as is well-known in the art.

For employment against vaginal infections, topical carriers affording maximum distribution of the active agent are preferred, e.g.:

Vaginal Creams a. Glycerol monostearate
   Corn oil
   Glycerine
   Benzoic acid
   Glutamic acid
   Water
b. Glycerine
   Ethyl alcohol
   Liquid petrolatum
   Polyethylene glycol ether: fatty alcohol complex
   Paraben preservatives
   Water Vaginal Suppositories a. Lactose
   Polyethylene glycol 400
   Polysorbate 80
   Polyethylene glycol 4000
   Glycerine
   Lactic acid
b. Polyethylene glycol
   Polyoxyethylene palmitate
   Lactic acid Topical vehicles for vaginal applications are pH-adjusted to the acid conditions under which normal bacteria flourish, so as not to debilitate body defense mechanisms. The art-skilled, of course, are well aware of this and other considerations involved in topical deployment of antiviral agents.

The topical preparations contain effective virus inhibiting proportions of the active agent, e.g., from about 0.01% to about 10% by weight of the total weight of the composition, preferably 0.025% to 1%, most preferably from 0.025% to 0.1% by weight. Up to about 10% by weight may be employed in the treatment of recalcitrant conditions. The quantity of the other ingredients in such preparations, of course, are commensurate with the quantities of such ingredients as normally used and determination of appropriate formulation is readily within the ability of the art-skilled given the disclosure herein.

It should be noted that the form in which the antiviral agent is administered, of course, will depend upon the particular virus infection being treated. For example, if the infection is caused by influenza or other respiratory virus and has manifested itself in the upper respiratory tract, the preferred mode of treatment will be the described aerosol nasal spray since this would deliver most effectively the agent to the site of the infection. Oral or injection therapy may be indicated, depending on the severity of the infection. If the infection appears to be a lower respiratory infection, or other systemic virus infection, the preferred mode of treatment would be orally or by injection. If the infection is of a topical nature, such as herpes labialis (cold sore, fever blister), herpes genitalis (viral infection of the penis or of the vaginal area), herpes zoster (shingles), varicella (chickenpox), exzema herpeticum, herpes dermatitis, etc., the appropriate application would be by topical application as described above, possibly combined with oral treatment or injection therapy, also as described above.

By way of illustration only, the following specific formulations of topical applications are offered.

| Ointment (% by Wt) | Cream (% by Wt) | Solution (% by Wt) |
|---|---|---|
| 1.0% Antiviral agent 99.0% Plastibase | 1.0% Antiviral agent 99.0% Vanishing cream consisting of .27% methyl paraben USP, .03% propyl paraben USP, 10% spermaceti USP, 1% sodium lauryl sulfate USP, 10% stearyl alcohol USP, 3% cetyl alcohol NF, 10% glycerin, and deionized water, q.s. | 1.0% Antiviral agent 99.0% topical solution consisting of 1.4% polyvinyl alcohol in deionized purified water. |

EXAMPLE VI

Specific antiviral activity of each of the triazoles of this invention has been demonstrated. They were tested for activity using the virus-induced cytopathogenic effect (CPE) method of Sidwell, et al., (Applied Microbiology 22:797–801, 1971). Briefly, the CPE procedure includes the dissolution of the antiviral agent in a cell culture medium consisting of vitamins, amino acids, serum, buffer, penicillin, streptomycin and indicator dye in water. The virus suspended in the cell culture medium was added to an established monolayer of KB cells, and an equal volume of the antiviral agent was then added within 15 minutes. The infected treated cells were graded following microscopic examination. Controls for each experiment include cell controls (cells and cell culture medium only), virus controls (cells and virus and cell culture medium) and toxicity controls (cells and chemical and cell culture medium). The virus rating (VR) system of Sidwell et al, described in Applied Microbiology, supra, was used to evaluate the degree of significance of CPE inhibition. A VR greater than 0.5 is indicative of significant antiviral activity and a VR of less than 0.5 suggests slight antiviral activity.

In experiments with measles virus, the above method was altered in that the infected cells were covered with an agar-serum-bicarbonate overlay containing the antiviral compounds so that viral plaques could be discerned. These plaques were strained with neutral red dye on day 4 and counted, with any reduction in plaque number resulting from exposure to the antiviral compound determined. The methodology for the experiment is as described by Wear et al (*Exptl. and Molecular Pathol.* 9:405–417, 1968).

The results of these antiviral experiments are set forth in Table 1.

TABLE 1

Comparative Antiviral Activity of 1,2,4-Triazole-3-carboxamide (1), 1,2,4,-Triazole-3-thiocarboxamide (2), and 1-β-D-Ribofuranosyl-1,2,4-triazole-3-carboxamide (3), in Cell Culture Systems.

| Virus | Virus Rating | | |
|---|---|---|---|
|  | Compd 1 | Compd 2 | Compd 3 |
| Type 1 Herpes | 0.6–0.9 | 0.4–0.8 | 1.0–1.5 |
| Type 2 Herpes | 0.4 | 0.3 | 1.3 |
| Vaccinia | 0.8 | 0.5 | 0.9–1.0 |
| Type 1A Rhino | 0.4–0.5 | 0.2–0.4 | 0.6 |
| Type 13 Rhino | 0.3 | 0.4 | 0.5 |
| Type 8 Rhino | 0.2 | 0.3 | 0.8 |
| Type 56 Rhino | 0.3 | 0.4 | 0.9 |
| Type 3 Parainfluenza | 0.5–0.7 | 0.2–0.4 | 0.6–1.0 |

| Virus | Compd Concentration (μg/ml) | % Plaque Inhibition | | |
|---|---|---|---|---|
|  |  | Compd 1 | Compd 2 | Compd 3 |
| Measles | 500 | 99 | 100 | 100 |
|  | 100 | 97 | 98 | 94 |
|  | 20 | 34 | 5 | 30 |

EXAMPLE VII

Each of the antiviral agents were tested for effectiveness against influenza $A_2$ infections in mice. Young adult mice were exposed to an aerosol of influenza $A_2$ virus in sufficient quantity to cause approximately 65% of the animals to die within 8 to 13 days. Groups were treated intraperitoneally with varying concentrations of the compounds suspended in saline twice daily for 6 to 9 days beginning 4 hours previrus exposure. Controls included virus controls (exposed to virus but treated with saline only), toxicity controls (sham-infected with virus diluent and treated with test compound), and normal controls (uninfected, untreated). Animals dying during the experiment were noted daily, and the lungs of all surviving mice were removed on day 25 and graded on a scale of 0 to 4 for the degree of viral consolidation occurring. The lungs were then pooled in the appropriate groups and homogenized in 15 ml of phosphate buffered saline (PBS, pH 7.2, 0.2M $PO_4$, 0.15M NaCl). The homogenized lung preparation was centrifuged at 1500 rpm for 15 minutes, diluted in two-fold dilutions in PBS, and an equal volume of 0.5% guinea pig red blood cells was added to each dilution. The extent of red cell agglutination, which would be a measure of virus in the lungs, was recorded after a 45 minute incubation at room temperature. This red cell agglutination was expressed as hemagglutinin (HA) titer per milliliter.

The results of these animal experiments, shown in Table 2, reflect the fact that each compound significantly lessened the severity of the viral disease using each parameter indicated.

TABLE 2

EFFECT OF 1,2,4-TRIAZOLE-3-CARBOXAMIDE (1), 1,2,4-TRIAZOLE-3-THIOCARBOXAMIDE (2), and 1-β-D-RIBOFURANOSYL-1,2,4-TRIAZOLE-3-CARBOXAMIDE (3) ON INFLUENZA $A_2$ VIRUS-INDUCED MORTALITY IN MICE

Host: Female Swiss Mice (15–17 g)     Route of Treatment: Intraperitoneal
Virus Dose: 3.2 $LD_{50}$
Route of Virus Inoculation: Aerosol
Observation Period: 21 Days

| Compound | Dose (mg/kg/day) | Description | Treatment[a] Schedule | Survivors Per Total | MST (Days) | Average Lung[b] Consolidation | HA Titer[c] Per ml |
|---|---|---|---|---|---|---|---|
|   | 0 | Saline + Virus | 1 | 7/20 | 11.7 | 3.7 | 1:64 |
| 1 | 1000 | Drug + Virus | 1 | 8/10 ($p<0.05$)[d] | 15 ($p<0.001$)[e] | 2.0 | 1.3 |
|   |   | Drug + MEM | 1 | 5/5 | >21 | n.d. | n.d. |
|   | 500 | Drug + Virus | 1 | 7/10 ($p<0.1$) | 12.0 ($p<0.05$) | 2.5 | 1:16 |
|   |   | Drug + MEM | 1 | 5/5 | >21.0 | n.d. | n.d. |
|   | 250 | Drug + Virus | 1 | 8/10 ($p<0.05$) | 17.5 ($p<0.001$) | 1.4 | 1:8 |
|   |   | Drug + MEM | 1 | 5/5 | >21.0 | n.d. | n.d. |
| 2 | 1000 | Drug + Virus | 2 | 3/10 ($p>0.3$) | 8.3 | 3.7 | 1:8 |
|   |   | Drug + MEM | 2 | 0/5 | 4.2 | n.d. | n.d |
|   | 500 | Drug + Virus | 3 | 5/10 ($p>0.3$) | 7.6 | 2.2 | 1:8 |
|   |   | Drug + MEM | 3 | 4/5 | 9.0 | 2.0 | 0 |
|   | 250 | Drug + Virus | 3 | 6/10 ($p<0.2$) | 9.2 | 3.6 | 1:16 |
|   |   | Drug + MEM | 3 | 5/5 | >21.0 | 0.5 | 0 |
|   | 75 | Drug + Virus | 1 | 10/10 ($p<0.001$) | >21.0 | 1.0 | Not done |
|   |   | Drug + MEM | 1 | 5/5 |   | n.d. |   |
|   | 37.5 | Drug + Virus | 1 | 10/10 ($p<0.001$) | >21.0 | 1.0 | Not done |
|   |   | Drug + MEM | 1 | 5/5 |   | n.d. |   |

[a]Treatment Schedule:
1. Drug administered twice a day for 9 days beginning 4 hr pre- and 4 hr post-infection.
2. Drug administered twice a day for 6 days beginning 4 hr pre- and 4 hr post-infection.
3. Drug administered twice a day beginning 4 hr pre- and 4 hr post-infection until Day 5, and once a day at half the dosage, beginning Day 6 for 3 additional days.

[b]Extent of lung consolidation in mice on Day 25 post-infection. A scale of 0–4 used to denote lung consolidation from 0–100%, n.d. = not done.
[c]Hemagglutinin titer in lung homogenates from 4 mice sacrificed on Day 25 post-infection.
[d]P = Probability (Chi Square analysis)
[e]P = Probability (t test)

It will be appreciated from Examples IV and V that both Compounds 1 and 2 have a spectrum of antiviral activity and are particularly effective against influenza virus. Relative cytotoxicity studies indicate slight alteration in a cell structure, with Compound 1 causing slight alteration in cell structure at 32 through 1000 μg/ml levels and 2 causing similar alterations in concentrations down to 1 μg/ml. Each compound was relatively insoluble in the aqueous medium used and although the antiviral activity was possibly limited slightly in cell culture, this relative loss of solubility did not unduly restrict the antiviral activity in the animal experiments.

In animal toxicity experiments, Compound 1 was nontoxic to mice when used in concentrations as high as 1000 mg/kg/day administered intraperitoneally twice daily for 9 days, whereas Compound 2 was moderately toxic as evidenced by weight loss and death in concentrations as low as 250 mg/kg/day administered by the same treatment regimen.

It should also be noted that the antiviral activity of 1,2,4-triazole-3-carboxamide may thus be due to its enzymatic conversion by the host to 1-β-D-ribofuranosyl-1,2,4-triazole-3-carboxamide. In any event, such enzymatic conversion provides a procedure of synthesis of 1-β-D-ribofuranosyl-1,2,4-triazole-3-carboxamide. This enzyme may be a purified protein or may be present in actively metabolizing bacterial or fungal cells. Being present in actively metabolizing bacterial or fungal cells it is expected that fermentation processes using these cells or mutants of these cells may lead to the production of 1-β-D-ribofuranosyl-1,2,4-triazole-3-carboxamide from 1,2,4-triazole-3-carboxamide.

We claim:

1. A process of preparing 1-β-D-ribofuranosyl-1,2,4-triazole-3-carboxamide in which 1,2,4-triazole-3-carboxamide is reacted with the enzyme nucleoside phosphorylase in the presence of ribose-1-phosphate at a pH of from about 5 to about 9 and a temperature of from about 0° to about 50°C.

2. The process of claim 1 in which said enzyme is utilized a concentration of about 0.015 to about 0.75 mg/ml.

3. The process of claim 2 in which the triazole-3-carboxamide is utilized in a concentration of at least about $5\times10^{-5}$ M and said ribose-1-phosphate at a concentration of at least about $2\times10^{-5}$ M.

4. The process of claim 2 in which the pH is about 7 to about 8 and the temperature from about 25° to about 35°C.

5. The process of claim 4 in which the concentration of said enzyme is about 0.15 mg/ml.

* * * * *